United States Patent [19]

Saunier et al.

[11] Patent Number: 5,679,029
[45] Date of Patent: Oct. 21, 1997

[54] CLAMP FOR ELECTROSURGICAL DISPERSIVE ELECTRODE

[75] Inventors: Robert G. Saunier, North St. Paul; Craig D. Oster, Oakdale, both of Minn.

[73] Assignee: Minnesota Mining and Manufacturing Company, St. Paul, Minn.

[21] Appl. No.: 655,800

[22] Filed: May 30, 1996

[51] Int. Cl.⁶ .................................................. H01R 4/28
[52] U.S. Cl. ........................................ 439/725; 439/909
[58] Field of Search ...................... 439/725, 838, 439/864, 909

[56] References Cited

U.S. PATENT DOCUMENTS

| | | | |
|---|---|---|---|
| 3,895,635 | 7/1975 | Justus et al. | 439/909 |
| 4,061,408 | 12/1977 | Bast et al. | 339/75 R |
| 4,555,155 | 11/1985 | Drake | 339/61 R |
| 4,700,997 | 10/1987 | Strand | 439/372 |
| 4,768,969 | 9/1988 | Bauer et al. | 439/725 |
| 4,842,558 | 6/1989 | Strand | 439/863 |
| 4,952,177 | 8/1990 | Drake et al. | 439/828 |
| 5,407,368 | 4/1995 | Strand et al. | 439/729 |
| 5,454,739 | 10/1995 | Strand | 439/729 |

*Primary Examiner*—Gary F. Paumen
*Assistant Examiner*—Tho Dac Ta
*Attorney, Agent, or Firm*—Gary L. Griswold; Walter N. Kirn; John H. Hornickel

[57] ABSTRACT

A clamp for a dispersive electrode is disclosed. The clamp includes (a) a housing having an exterior surface, an interior surface being formed within the housing for receiving projecting tabs of the electrode, and a slot in the housing disposed between the exterior surface and the interior surface; (b) a mechanism for releasably engaging the tabs at the interior surface; (c) a reinforcement on the releasably engagement means; and (d) a slot on the exterior surface of the housing having a shape matching the reinforcement.

1 Claim, 1 Drawing Sheet

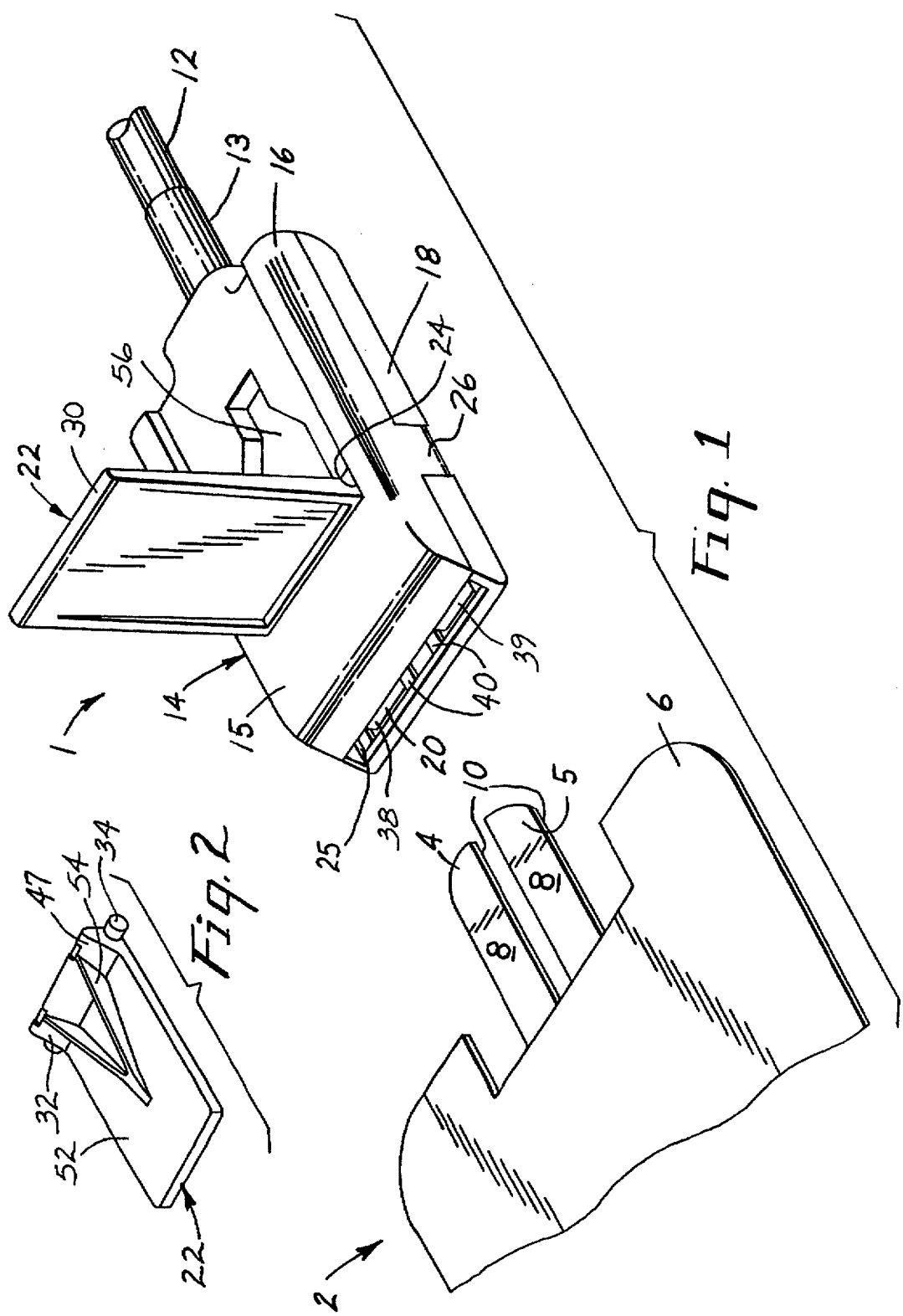

5,679,029

CLAMP FOR ELECTROSURGICAL DISPERSIVE ELECTRODE

FIELD OF INVENTION

This invention relates to clamps for dispersive electrodes.

BACKGROUND OF INVENTION

Biomedical electrodes are used in a variety of applications and are configured to operate according to the size, type, and direction of current flowing into or out of a body of a patient.

Dispersive electrodes are used in electrosurgery. In modern surgical practice there are many times when electrosurgery is more preferable than the use of the traditional scalpel. In electrosurgery, cutting is performed by an intense electrical current passing through a cutting electrode. The surgeon directs this current to exactly where cutting is required by wielding the cutting electrode, which because of its cylindrical shape and the way it is held in the hand is commonly called an "electrosurgical pencil". By activating controls which change the characteristics of the electrical current being sent to the pencil by an electrosurgical generator, the surgeon can use the pencil either to cut or to coagulate areas of bleeding. This makes electrosurgery particularly convenient when surgery requiring extra control of blood loss is being performed. Because of concerns to minimize the transmissions of blood-borne illnesses between health care patients and health care providers, in both directions, electrosurgery is becoming increasingly important.

In electrosurgery, as in all situations where electrical current is flowing, a complete circuit must be provided to and from the current source. In this case, the current that enters the body at the pencil must leave it in another place and return to the generator. It will readily be appreciated that when current enough to deliberately cut is brought to the body of a patient in one place, great care must be taken that unintentional damage is not also done to the patient at the location where that current is leaving the body. The task of collecting the return current safely is performed by a dispersive electrode.

A dispersive electrode performs this task by providing a large surface area through which the current can pass; the same current which was at cutting intensity when focused at the small surface area at the tip of the pencil is relatively harmless, with the goal of being painless to the patient, when spread out over the large surface area of the dispersive electrode.

Between the dispersive electrode and the electrosurgical generator, the typical manner to complete the circuit is to electrically connect the end of the dispersive electrode to a clamp connected to an electrical wire ending in a plug compatible with the electrosurgical generator.

Any tendency toward disconnection of the clamp from the dispersive electrode is critical to maintenance of the electrical circuit.

Some clamps are known to those skilled in the art. Two examples of clamps are represented by U.S. Pat. No. 4,061,408 (Bast et al.) and U.S. Pat. No. 4,952,177 (Drake et al.). Commercially available clamps related to such patents are available from 3M Health Care of Minnesota Mining and Manufacturing Company of St. Paul, Minn.

Smaller size clamps, known as clips, are used for smaller biomedical electrodes used to receive electrical signals from a patient's body. Examples of such clips are represented by U.S. Pat. No. 4,555,155 (Drake et al.); U.S. Pat. No. 4,700,997 (Strand et al.); U.S. Pat. No. 4,842,558 (Strand et al.); U.S. Pat. No. 5,407,368 (Strand); and U.S. Pat. No. 5,454,739 (Strand).

While clamps and clips serve similar purposes to complete an electrical connection, the dispersive electrode used with a clamp differs from an electrocardiographic electrode used with a clip, in that the dispersive electrode can have two different electrically conductive surfaces for Contact Quality Monitoring ("CQM") circuitry that tests continued adequate electrical connection of the electrode with the clamp to avoid burning skin of the patient.

SUMMARY OF INVENTION

The present invention provides a clamp that has different features from that found in prior clamps or clips.

The clamp for an electrosurgical electrode comprises (a) a housing having an exterior surface, an interior surface being formed within the housing for receiving projecting tabs of the electrode, and a slot in the housing disposed between the exterior surface and the interior surface; (b) means for releasably engaging the tabs at the interior surface; (c) a reinforcement on the releasably engagement means; and (d) a slot on the exterior surface of the housing having a shape matching the reinforcement.

A feature of the present invention is a reinforcement of the lever of the clamp.

Another feature of the present invention is a slot in the upper surface of the clamp that matches the shape of the reinforcement of the lever and also permits viewing of the placement of the dispersive electrode into the clamp.

BRIEF DESCRIPTION OF DRAWINGS

FIG. 1 is a perspective view of a clamp of the present invention, along with a portion of a CQM dispersive electrode known in the art, particularly showing the plurality of the projecting tabs entering the clamp.

FIG. 2 is a perspective view of the undersurface of the lever for the clamp of the present invention.

EMBODIMENTS OF INVENTION

Referring to FIG. 1, the clamp 1 is shown engaging the split-plate dispersive electrode 2 as a portion of the electrosurgical generating system (not shown).

The split-plate dispersive electrode 2 has two separate tabs, 4 and 5, projecting from a backing 6 of the electrode 2. Tabs 4 and 5 have opposed surfaces. One surface is an insulated surface 8 shown in FIG. 1 as the upper surface on both tabs 4 and 5. The opposing surface is a conductive surface 10, shown in FIG. 1 as the opposed under surface of tabs 4 and 5.

The clamp 1 is connected to a cable 12 having a strain relief 13 engaging a clamp housing 14 having an exterior surface 15. The cable 12 is connected to the electro-surgical generator (not shown) which may require an electrical adaptor for proper electrical connection.

The housing 14 is divided into a first cover 16 and a second cover 18. The housing 14 is configured to have a tabs receiving slot 20 at a point on its exterior surface 15 of joinder between first cover 16 and second cover 18 to allow insertion of the tabs 4 into the housing 14.

A lever 22 in communication with interior surfaces 25 of the housing 14 extends through a lever slot 24 on the exterior surface 15 of the first cover 16.

The first cover 16 and the second cover 18 are secured by latches 26 received in notches (not shown) in the housing 14 on exterior surface 15 not adjacent to the tabs receiving slot 20.

The lever 22 is composed of a handle 30, a pivot portion 32, from which extend oppositely disposed pins 34. Pins 34 reside in complimentary grooves on the second cover 18 of the housing 14.

On the interior surface 25 of housing 14, two receiving electrical contact strips 38 and 39 are shown in their restrained positions separated from one another within second cover 18 as held laterally in place by fingers 40. In this embodiment, strips 38 and 39 are generally U-shaped flat springs configured to receive tabs 4 and 5, respectively.

When tabs 4 and 5 are inserted into clamp 1 through slot 20, the tabs must be releasably engaged to maintain continuous electrical connection with the separated electrical contact strips 38 and 39. The means for releasably engaging the tabs 4 are composed of the lever 22 having the handle 30, pins 34 on pivot portion 32 and rotating in grooves, all previously described. The means further include a cam ridge 47.

As seen in FIG. 2, lever 22 has an undersurface 52 having a reinforcement wishbone 54 extending from undersurface 52 and cam ridge 47. To accommodate the shape of wishbone protruding from undersurface 52 of lever 22, first cover 16 also contains a wishbone slot 56 adjoining lever slot 24.

When lever 22 is closed toward first cover 16, reinforcement wishbone 54 projects into wishbone slot 56.

Wishbone slot 56 also serves the feature of permitting the placement of tabs 4 and 5 of electrode 2 to be viewed as the tabs 4 and 5 are inserted into slot 20 of clamp 1.

While embodiments of the invention have been disclosed, the claims of the invention follow.

What is claimed is:

1. A clamp for an electrosurgical electrode, comprising:
   (a) a housing having an exterior surface, an interior surface being formed within the housing for receiving projecting tabs of the electrode, and a tab receiving slot in the housing disposed between the exterior surface and the interior surface;
   (b) means for releasably engaging the tabs at the interior surface, the means including a lever with a cam thereon;
   (c) a wishbone shaped reinforcement on the lever, supporting but additional to the cam; and
   (d) a wishbone shaped tab viewing slot on the exterior surface of the housing.

* * * * *